(12) United States Patent
Krietzman (10) Patent No.: US 11,534,560 B2
(45) Date of Patent: Dec. 27, 2022

(54) AROMATHERAPY CONVECTION HEATING CONTROL SYSTEM

(71) Applicant: Mark Krietzman, Palos Verdes Estates, CA (US)

(72) Inventor: Mark Krietzman, Palos Verdes Estates, CA (US)

( * ) Notice: Subject to any disclaimer, the term of this patent is extended or adjusted under 35 U.S.C. 154(b) by 315 days.

(21) Appl. No.: 15/930,265

(22) Filed: May 12, 2020

(65) Prior Publication Data

US 2021/0346616 A1    Nov. 11, 2021

Related U.S. Application Data (60) Provisional application No. 63/020,871, filed on May 6, 2020.

(51) Int. Cl.
*A61M 11/04* (2006.01)

(52) U.S. Cl.
CPC ... *A61M 11/042* (2014.02); *A61M 2205/3327* (2013.01); *A61M 2205/3368* (2013.01); *A61M 2205/587* (2013.01)

(58) Field of Classification Search
CPC ........ A61M 11/042; A61M 2205/3327; A61M 2205/3368; A61M 2205/587; A61M 15/0021; A61M 15/0025; A61M 2205/3592; A61M 2205/3633; A61M 2205/3653; A61M 2205/502; A61M 2205/505; A61M 2205/584; A61M 2205/8212; A61M 2205/8237; A61M 2209/04; A61M 15/08
See application file for complete search history.

(56) References Cited

U.S. PATENT DOCUMENTS

| | | | |
|---|---|---|---|
| 2018/0085551 A1* | 3/2018 | Krietzman | H05B 1/0252 |
| 2018/0289909 A1* | 10/2018 | Lindars | A61M 15/06 |
| 2019/0328042 A1* | 10/2019 | Krietzman | H05B 1/0225 |
| 2021/0001063 A1* | 1/2021 | Benson | A61M 11/042 |
| 2021/0346616 A1* | 11/2021 | Krietzman | A61M 11/042 |

* cited by examiner

*Primary Examiner* — Truc T Nguyen
(74) *Attorney, Agent, or Firm* — Mark Krietzman (57) ABSTRACT

Disclosed herein are aspects of portable vaporizers to deliver aliquots of heated air to material in a unitary furnace. The furnace is multipurposed reducing heat loss, air leakage and delays in availability of air aliquots at the proper temperature for use. By dividing the unitary furnace with an air permeable divider and placing material in the chamber a controller selectively providing electrical power to a heating element configured to heat air in at least an upper region of the unitary furnace. Upon application of suction to the fluid passage heated air passes into the material and vaporizes organic oils in the material and said heating a volume of air inside a unitary furnace vaporized material can be withdrawn from the fluid passage.

14 Claims, 5 Drawing Sheets

AROMATHERAPY CONVECTION HEATING CONTROL SYSTEM

BACKGROUND OF THE DISCLOSURE

Field of the Disclosure

The present disclosure relates generally to vaporizing oils without combustion by way of heated aliquots of air in a unitary furnace and material chamber containing organic plant material.

Related Art

Vaporizer for plant-based materials and essential oils and exist. Vaporizers allow aroma therapy or inhalation. Vaporizers which allow inhalation from a fluid pathway whereby gas containing the vapor without combustion by products through a fluid pathway from source of vapor to exists. Herbs and botanicals have been known in the art to be vaporized or burned to release organic material in the form of inhalable material.

Lavender vaporizes at 260° F. Tobacco vaporizes between 257° F. to 302° F.; Green tea vaporizes between about 175° C. to 185° C.; Valerian vaporizes at about 235° C.; Chamomile used to aid in the relief of anxiety vaporizes at about 380° F.; Peppermint vaporizes at about 255° F. Peppermint is also known to ease symptoms of allergies and asthma, in addition to alleviating some of the side effects that come along with the common cold or a sinus infection. Cannabis has a range at which it can be heated to release different cannabinoids as vapor without burning the organic material. From below 200 F to about 420 F.

In the following description of examples of implementations, reference is made to the accompanying drawings that form a part hereof, and which show, by way of illustration, specific implementations of the present disclosure that may be utilized. Other implementations may be utilized, and structural changes may be made without departing from the scope of the present disclosure.

DISCLOSURE

Aspects of portable aromatherapy devices and methods to heat and/or deliver a predetermined aliquot of air at a predetermined temperature or temperature range to a material are disclosed. Aspects of portable aromatherapy devices and methods to heat and/or deliver a predetermined aliquot of air at a predetermined temperature or temperature range to a material and produce vapor from an essential oil are disclosed.

A unitary furnace and material chamber is configured to provide controlled aliquots of heated air to plant material and minimize or avoid combustion is disclosed and aspects related to temperature control. It will be appreciated that the overheating of plant based material will cause combustion and release toxins and chemicals which are ameliorated via vaporizing the material to precisely control temperatures.

It is appreciated by those skilled in the art that some of the circuits, components, controllers, modules, and/or devices of the system disclosed in the present application are described as being in signal communication with each other, where signal communication refers to any type of communication and/or connection between the circuits, components, modules, and/or devices that allows a circuit, component, module, and/or device to pass and/or receive signals and/or information from another circuit, component, module, and/or device. The communication and/or connection may be along any signal path between the circuits, components, modules, and/or devices that allows signals and/or information to pass from one circuit, component, module, and/or device to another and includes wireless or wired signal paths. The signal paths may be physical such as, for example, conductive wires, electromagnetic wave guides, attached and/or electromagnetic or mechanically coupled terminals, semi-conductive or dielectric materials or devices, or other similar physical connections or couplings. Additionally, signal paths may be non-physical such as free-space (in the case of electromagnetic propagation) or information paths through digital components where communication information is passed from one circuit, component, module, and/or device to another in varying analog and/or digital formats without passing through a direct electromagnetic connection. These information paths may also include analog-to-digital conversions ("ADC"), digital-to-analog ("DAC") conversions, data transformations such as, for example, fast Fourier transforms ("FFTs"), time-to-frequency conversations, frequency-to-time conversions, database mapping, signal processing steps, coding, modulations, demodulations, etc. The controller devices and smart devices disclosed herein operate with memory and processors whereby code is executed during processes to transform data, the computing devices run on a processor (such as, for example, controller or other processor that is not shown) which may include a central processing unit ("CPU"), digital signal processor ("DSP"), application specific integrated circuit ("ASIC"), field programmable gate array ("FPGA"), microprocessor, etc. Alternatively, portions DCA devices may also be or include hardware devices such as logic circuitry, a CPU, a DSP, ASIC, FPGA, etc. and may include hardware and software capable of receiving and sending information.

Aspects of some exemplary implementations of systems, device and methods associated with vaporization of plant materials disclosed herein include a portable aromatherapy vaporizing system with unitary furnace and material chamber with a power supply supplying power to a heating system visa vie a controller configured to heat air in the unitary furnace to a predetermined temperature and continue to heat said air during an inhalation which draws air external to the unitary furnace into the unitary furnace. The unitary furnace has an open top and bottom end. Generally, the unitary furnace and material chamber have four regions (i) a material region "CR", (ii) an upper region "UR", (iii) a mid region "MR", and a lower region "LR". A material chamber is formed by dividing the unitary furnace with an air permeable divider between the material region and the upper furnace. The bottom of the unitary furnace is partially closed or sealed off the with a floor region. Within the lower and mid regions of the unitary furnace is one or more heating elements. With the main area generating heat in the mid region. In some instance a temperature sensor is place, mounted or fixed in close proximity to the floor within the unitary furnace. A controller in signal communication with at least the sensor, heating element, power supply and an on/off control is provided and at least a portion of the air used during vaporization of material enters the bottom of the unitary furnace from the air from the insulation zone "AIZ".

Aspects of some exemplary implementations of systems, device and methods associated with vaporization of plant materials disclosed herein include a portable aromatherapy vaporizing system with unitary furnace and material chamber with a power supply supplying power to a heating system visa vie a controller configured to heat air in the unitary furnace to a predetermined temperature and continue to heat said air during an inhalation which draws air external to the unitary furnace into the unitary furnace. The unitary furnace and associated heating element, controller, power supply and the like are within a generally hollow body with an open top at least the heating system and power supply are within the body. The unitary furnace has an open top and bottom end. A cover which partially seals the open top of the body and the open top of the body and open top of the unitary furnace are coaxially aligned. The bottom of the unitary furnace is partially closed or sealed off the with a floor region. Within a mid region of the unitary furnace is a heating elements. In some instance a temperature sensor is place, mounted or fixed in close proximity to the floor within the unitary furnace. A controller in signal communication with at least the sensor, heating element, power supply and an on/off control is provided. In some instances a cover with an inner annular wall and is configured to removably partially seal and fits over the open top of the body and the top of the unitary convection furnace and material chamber. In some instances a fluid passage through the cover has a first interface profile formed at the fluid passage and a user interface with a second interface profile is configured to fluidly connect to the cover.

At least one illumination communication means in signal communication with the controller is in some implementations and is configured to produce an illumination visible on the exterior of the body. To activate the vaporizing system an on/off control is in signal communication with the controller wherein pushing the on/off control initiates a heating cycle. In some instances a storage module interface catch is formed on the cover and, a storage container configured to reversibly mate with the interface catch by way of a storage module latch is included.

Aspects of some exemplary implementations of systems, device and methods associated with vaporization of plant materials to deliver aliquots of heated air to material in a unitary furnace, to material. A material region is formed by dividing a unitary furnace with an air permeable divider and placing material therein. The bottom of the unitary furnace is partially blocked, restricted or sealed with a floor configured to allow air to be drawn into the bottom of the unitary furnace. To withdraw vapor the top of the unitary furnace is partially closed or seal with a cover having a fluid passage in fluid communication with the unitary furnace. A controller selectively provides electrical power to a heating element within the unitary furnace configured to heat air in at least an upper region of the unitary furnace. By applying suction to the fluid passage heated air passes into the material and vaporizes organic oils in the material and said heating a volume of air inside a unitary furnace.

In some instances a temperature sensor in signal communication with the controller fixed in close proximity to the floor within the unitary furnace and, the controller controls the electrical power supplied to the heating element at least in part based on the temperature sensor input to the controller. In some instances a temperature sensor the controller selectively signals the user with LED (304) illumination passing through a lens. The signal to the user displays status of a state of the heating and vaporizing system.

The following description of examples of implementations, reference is made to the accompanying drawings that form a part hereof, and which show, by way of illustration, specific implementations of the present disclosure that may be utilized. Other implementations may be utilized, and structural changes may be made without departing from the scope of the present disclosure.

FIGURES

The disclosure may be better understood by referring to the following figures. The components in the figures are not necessarily to scale, emphasis instead being placed upon illustrating the principles of the invention. In the figures, like reference numerals designate corresponding parts throughout the different views.

All descriptions and callouts in the Figures and all content therein are hereby incorporated by this reference as if fully set forth herein.

FURTHER DESCRIPTION

Disclosed herein are aspects, exemplary implementations Vaporizing plant material or extracts for inhalation of compounds therefrom is absent the by-products of combustion found in smoking (or combusting) plant material and is considered by many to be less harmful then combusting the same plant material.

Aspects of vaporizers, systems and methods of use involving utilizing temperature controlled heated air to release organic compounds from plant materials and extracts is disclosed. In some instances the furnace characteristics reduce power requirements for heating and/or reduce the parasitic heat losses.

In some instances the control system includes one or more of software, logic, sensors, LEDs, thermistors, thermocouples and controllers having hardware, memory and microprocessors to one or more of control, limit, warn about or prevent over heating of materials. In some instance the vaporizer includes Wi-Fi, Bluetooth or other wireless communication to a smart phone to allow an application on the smart phone to control heating parameters and/or monitor usage and performance. In some instance the vaporizer includes Wi-Fi, Bluetooth or other wireless communication to allow an application to control temperature settings.

The instant disclosure teaches aspects of vaporizers utilizing heated air flow (convection) via a unitary furnace to efficiently heat material (which includes one or more of concentrate, extract and plant material) in a chamber. The chamber is a portion of the unitary furnace. Testing demonstrated that the unitary furnace reduced at least one of heat losses to a separate material chamber, air leakage, start-up time for each use after the first use during a series of uses.

Figure 1A:
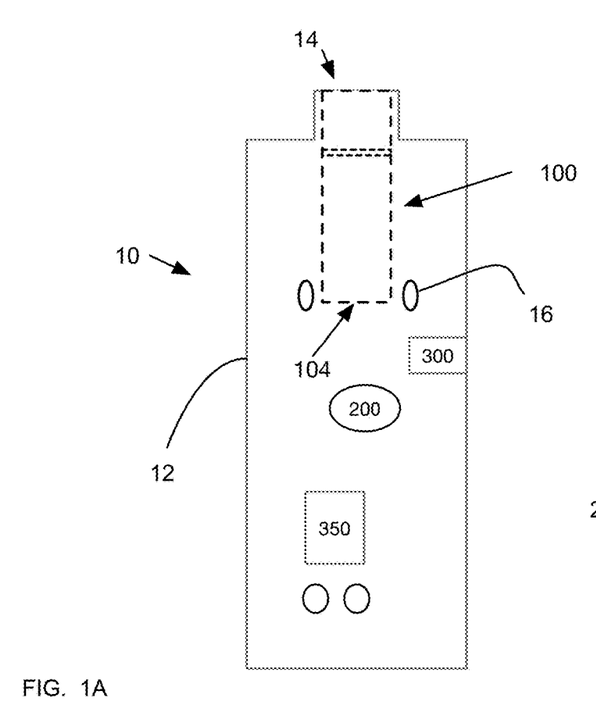
FIGS. 1A-1B illustrates aspects of main components of a convection vaporizer.
Figure 1B:
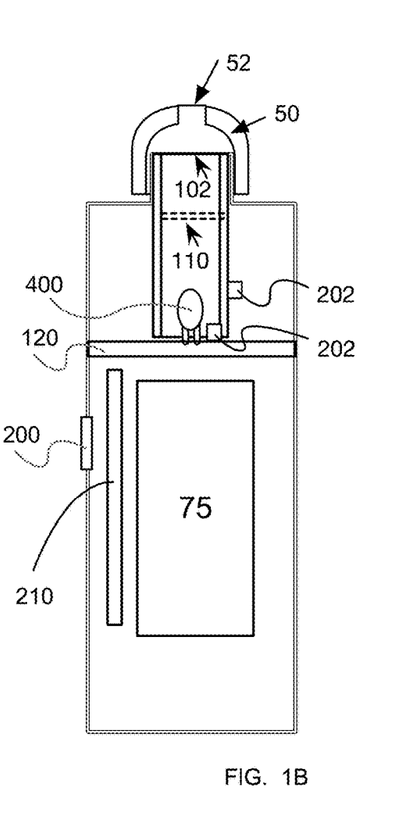

FIGS. 1A and 1B illustrates a vaporizer 10 forming a body 12 with an open top 14 which is at least partially hollow having a unitary convection furnace and material chamber 100 therein (with convection heating—not shown in this figure) the unitary convection furnace and material chamber should be a heat insulator such as alumina ceramic, zircon, quartz glass or titanium and it has an open top 102 and an open bottom 104. In some instance the wall of the furnace are an insulator such as alumina or other ceramic and about 2 to about 4 mm in thickness. If stainless steel is utilized the furnace wall is preferably less than 1 mm thick and more preferably less than 0.5 millimeters thick and most preferably less than 0.25 millimeters thick and a double walled vacuum insulated cylindrical. Suitable materials should have no harmful levels of outgassing at temperatures the furnace should be used. These materials include but are not limited to phenolic resins, aluminum, titanium, stainless steel, quartz glass, fused silica and ceramics. One or more air intake vents 16 are formed through the body and in fluid communication with the interior of the body. An on/off switch 200 is accessible on the exterior of the body and an illuminated communication means 300 such as a LED, laser, electroluminescent device is visible on the exterior of the body. In this chamber mates directly into the open top 402 of the furnace.

FIG. 1B illustrates an interior view of the vaporizer of FIG. 1A with a cutaway showing the unitary convection furnace and material chamber 100 configured with an air permeable divider 110 to divide the unitary convection furnace and material chamber and form the material holding region below the open top 102. A heating means 400 is positioned in the bottom portion of the unitary convection furnace and material chamber near the open bottom 104. A cover 50 partially seals and fits over the open top 14 of the body. The cover has a fluid passage 52 configure to allow vapor to be withdrawn. A floor 120 is positioned near the bottom end 104 of the unitary convection furnace and material chamber. A battery power supply 75 is placed within the body. At least one controller 210 is placed within the controller and is in signal communication with at least the on/off switch, the battery and the heating means. The controller (also see FIG. 2) may also be in signal communication with the illumination communication means. One or more temperature sensor 202 such as a thermistor or other thermocouple are shown in thermal communication at or near the unitary convection furnace and material chamber. The temperature sensor are configured to be in signal communication with the controller which is configured to process and receive sensor data.

Colored illumination via the illuminated communication means such as light emitting diodes (LEDs) are useful for communications. The illuminated communication provide a visual language output, controlled by the controller, wherein the one or more printed circuit boards (PCB) "board" having the microprocessor controller 210 will also have memory and other components to support signal communication, heating, temperature control and input/output to control functions of the device. PCBs and controllers are well known in the art. Pulse width modulation (PWM) power management, temperature sensor inputs, memory, clock, and Wi-Fi connect ability are a non-exclusive list of PCB "board" components and functions. The controller controls one or more of color, strobe, frequency, intensity and movement of the illumination provided. In the case of LEDs the controller can turn some LEDs off or change color or selectively turn a series of LEDs on or off to show movement of areas of light to convey state of the device. A non-limiting, example of how the communication means and/or LEDs provide a user visual information or cues regarding a state of the system of vaporization and heating include a steady illumination communicates the aliquot of air to be delivered to the material is at a predetermined temperature and ready for a user to inhale to use. Flashing communicates the system is heating up. Alternatively red, green or blue can each be given a definition and the display of such a color corresponds with the definition.

Figure 2:
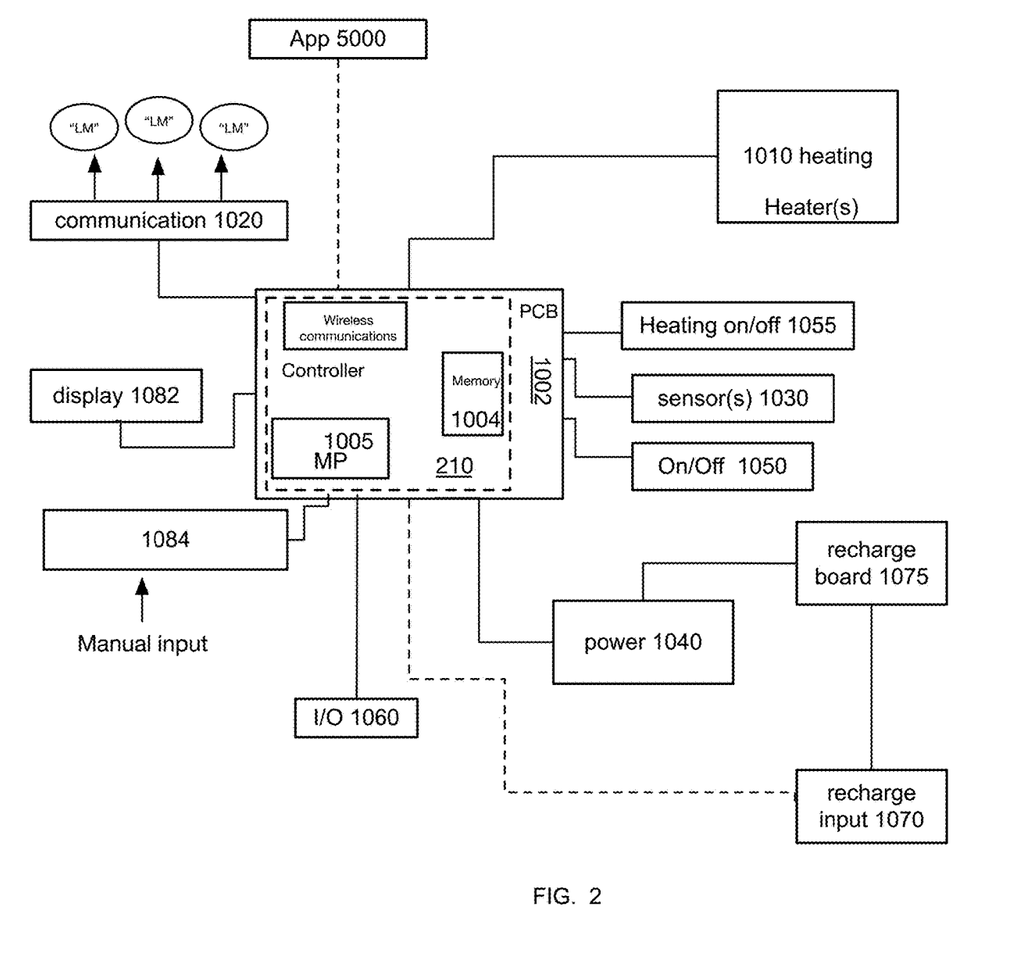
FIG. 2 illustrates a schematics of aspects of the control system of convection vaporizers.

FIG. 2 shows aspects of main components of a control, electrical and heating systems of exemplary implementations of a vaporizer device. A printed circuit board(s) (PCB) 1002 is the substrate of the "Controller" it contains memory 1004, processors 1005 and other components such as sensor input, outputs, the circuit components to control convection heating element(s) 1010 and communications 1020 including pulse width modulation for heating and inputs form sensors 1030. The board is also electrically or wirelessly in signal communication with and/or connected to:

1. A power supply 1040 which may be battery, or the onboard battery may be exchanged for a plug-in variation to supply power from a remote battery supply, plug in the wall supply or other electrical power generator. If the battery is on board the device a PCB with control functions 1075 can manage recharge and is electrically connected to the battery supply to recharge. Optionally the Controller may be configured to manage the recharge.

2. At least one convection heating element 1010 therein.

3. One or more sensors 1030 to monitor, report and provide data to the controller's microprocessor "MP" to control temperature of the system via control of power supplied to the convection heating elements.

4. A main power on/off switches 1050.

5. On or more heating on/off switches 1055.

6. One or more inputs and outputs for data transfer 1060, and/or charging 1070.

7. The recharge PCB 1075 with circuitry to control charge to batteries. The recharge board function may optionally be controlled by the controller.

8. The communications 1020 via illumination is controlled by the controller and turns off and on one or more lighting means LM as well as may adjust color, intensity, and frequency.

9. An optional display 350 such as a liquid crystal one may be configured on the outside of the body to show information about the device to a user.

10. Manual input from a user may be input from switches 1084 also accessible on the outside of the device.

11. An application 1090 on a computing device or smart phone can be in wireless signal communication with the controller via Bluetooth, nearfield, Wi-Fi such as 802.11xx chip or other wireless protocol which communicates wirelessly to view, adjust, or monitor temperature, battery usage, other operation and report operation and usage of the device.

FIGS. 3-5B illustrate aspects of implementations of aromatherapy convection vaporizers 2000 and aspects of modular encasements 3000 attachable to said vaporizers. The heat exchange systems disclosed herein is configured to use the latent head residue from usage of the convection device to heat up, dehumidify and dry out a portion of the air before it is introduced into the furnace. Heated air 2002 in the air insulation zone (AIZ) of a vaporizer and thus heat up and dehumidify the incoming air before it reaches the unitary convection furnace and material chamber 100. Many organic plant materials react differently to water vapor and by pre-drying the inflowing air supply, water vapor is reduced which passes through the furnace into the material being vaporized thus decreasing the effect of water vapor on said material and vapor compounds arising therefrom. Preheating and drying air also reduces energy needed to heat the incoming air as disclosed.

In some instances convection vaporizer may include removable storage to ameliorate smell associated with vaporizing material including smell or odor of resins and oils which may coat portions of the material chamber and fluid pathway, by storing the chamber, parts of fluid pathway, to avoid loss of parts or disassociation and/or store items.

FIGS. 3-5B shows aspects of convection vaporizers with unitary furnace and material chambers. The body 2001 is generally hollow, the bottom of the body 2002 is formed at least partially open. Affixed within the body inset from the bottom 2002 is a bottom plate 18 which partially seals the body's bottom. Shown support on that plate in a main power on/off switch 5002 and one or more input outputs such as date line and recharge connection 5004, these are in signal communications with the controller. The recharge input may be in signal communications with a recharge controller (PCB) 1075 or the controller 210. In this implementation a heating on/off switch 5006 is affixed on the exterior of the body and is in signal communication with the Controller 210. A battery power supply 75 is placed within the body and is in electrical communication with the recharge connection 5004 and the controller 210 which includes the necessary circuitry such as a mosfet for switching the power from battery supply to heating element per the microprocessor "MP" and software thereon. An A cover 50 with inner annular wall 55 reversible and partially seals and fits over the open top 14 of the body and the top 102 of the unitary convection furnace and material chamber. A gasket 56 inside the cover can be added to improve the seal. The top 102 of the unitary convection furnace and material chamber is surrounded with an insulator 150 to both fix it in place and provide a surface to seal against the cover. A screen 58 may be added to reduce any vaporizing material "M" passing from the device into the fluid passage 52 or the user interface 2100 which mounts into the fluid passage 52. The body a bottom 17, shown as partially open. An end plate 18 is shown below the battery power supply 75 and closing off the bottom of the base 10.

The unitary furnace serves multiple purposes. In this instance it provides a boundary to pass both collect an aliquot of heated air and to delivery that aliquot to the material "M" in the at a predetermined temperature sufficient to vaporize essential oils therein. The unitary furnace also contains an air permeable screen 110 which supports the material "M" at a preselected distance from the convection heating element 410. Via the heating process the unitary furnace in this embodiment is preferably one of 97% alumina or above ceramic, 98% alumina, 99% alumina or above, and quartz glass which is not a perfect insulator and therefore has some heat pass through its walls from the interior and exterior walls of the furnace (107 and 109 respectively) which is a loss. A catch (108) may be formed in the inside wall (107) of the unitary furnace configured to mate with the air permeable divider.

Air in the proximate area 420 surrounding the exterior of the unitary furnace in the air insulation zone "AIZ" is heated during use from the lost heat from the unitary furnace and that heating reduces humidity and preheats air in that region thereby reducing the power requirements to heat air entering the furnace to a preselected temperature. Further, the unitary furnace contains four zones during operation. The upper region "UR", mid region "MR" and lower region "LR" and material region "CR". The lower region LR is below the resistance heater and is fluidly connected to the incoming air from outside the unitary furnace which passes along the pathway of arrow 112 through a vent 105 into the unitary furnace and may also include air passing through the floor 120 through floor vent 121 these are the only access for incoming air. The floor is also the location of a temperature sensor 202 in this implementation it is fixed on or near the floor, in some instances it is placed 1 mm above the floor, in some instance it is placed 1.5 mm or less above the floor, in some instance it is placed 2 mm or less above the floor. In some instance it is placed 2.5 mm or less above the floor. In some instance it is placed 3 mm or less above the floor. In some instance it is placed 3.5 mm or less above the floor. In some instance it is placed 4 mm or less above the floor. In some instance it is placed 5 mm or less above the floor. In some instance it is placed 5.5 mm or less above the floor. In some instance it is placed 6 mm or less above the floor. In some instance it is placed 6.5 mm or less above the floor. In some instance it is placed 7 mm or less above the floor. In some instance it is placed 7.5 mm or less above the floor. In some instance it is placed 8 mm or less above the floor. In some instance it is placed 8.5 mm or less above the floor. In some instance it is placed 9 mm or less above the floor. In some instance it is placed 9.5 mm or less above the floor. In some instance it is placed 10 mm or less above the floor. In some instance it is placed 10.5 mm or less above the floor. In some instance it is placed 11 mm or less above the floor. In some instance it is placed 11.5 mm or less above the floor. The mid region MR is in close proximity to the resistance heating element no more than 5 mm above and 5 mm below. The upper region UR is above the mid region and ends at the bottom of the air permeable divider 110. The material region CR is the area of the unitary furnace above the air permeable divider and below the top of the unitary furnace.

Testing has demonstrated that a temperature sensor 202 located near the floor is a control for vaporization to achieve optimal vaporization. Optimal being the maximum release of vapor from the material with the minimum combustion. The temperature sensor is in signal communication with the controller whereby the temperature may be dynamically adjusted via a microprocessor using PWM to maintain predetermined or selected temperatures. By locating the sensor at the lower region LR of the furnace the sensor and controller heat an aliquot of air in the tubular furnace. The aliquot volume is a predetermined amount and should be in a range from 50 ml (milliliters) to 200 ml of air. In some instances greater than one of 25 ml, 30 ml, 40 ml, 50 ml, 60 ml, 70 ml, 80 ml, 90 ml, 100 ml, 110 ml, 120 ml, 130 ml, 140 ml, 150 ml, 160 ml, 170 ml, 180 ml, 190 ml and 200 ml. Upon inhalation the temperature sensor will register change as soon as the heated aliquot volume moves upward in the furnace and cooler air from outside the furnace is drawn in to the bottom of the furnace through vents. The sensor and controller then increase the power and heating during inhalation for more responsive temperature control. Conversely an additional temperature sensor 202 near the air permeable divider remains at temperature until the last of the aliquot has been drawn in thus creating a second date point to use in fine tuning the heating profile which measures the rate of temperature change at two point.

In practice the method of operation uses the resistance to airflow provided by the air permeable screen and the material in the material region CR to limit upward flow in the absence of suction or negative pressure supplied by inhalation at the user interface 2100. The user interface may be a ridged tube or hose, or it may be a flexible member each with a fluid pathway and configured to be fluidly connected to the top of the furnace. Accordingly, an aliquot of air is heated in the upper region UR which will eventually fill the unitary furnace and extend to the lower region LR. When the air reaches the temperature sensor in its predetermined location at the floor a predetermine aliquot of air heated to a predetermine level is available for vaporization and at that point the illuminated communication means 300 communicates to the user to inhale. Alternatively, if the user does not inhale the sensor will supply that information to the controller. The controller is configured to reduce heating if the aliquot of air heated to a predetermined temperature is reached unless or until the temperature changes or the system is timed out or shuts off thereby reduce the heating thereby saving power and preventing overheating. Because the vaporization is by convection, providing a predetermined aliquot of heated air improves temperature control and can prevent combustion associated with conduction vaporization.

The device delivers aliquots of heated air to material "M" by enclosing a volume of air within the unitary furnace beneath the material region (CR) by dividing the unitary furnace with an air permeable divider and placing material "M". By selectively heating the heating element via the controller and heating air in at least an upper region (UR) of the unitary furnace then applying suction to the fluid passage heated air passes into the material ("M") and vaporizes organic oils in the material and said vaporized material is withdrawn from the fluid passage. The temperature sensor placed near the floor of the device provides data to the controller allowing for the controller to adjust the heating as described herein.

The logic includes a timing sequence wherein when a cycle of heating is initiated the cycle raises the air in the temperature via the convection heating element either until the sensor data measures the upper threshold or until a time limit expires. Testing shows that sufficient latent heat remains in the furnace and heating element to provide some vaporization of cannabis oils for 10 or more seconds after the heating element is no longer supplied power at the end of a cycle. The controller is configured to display an illumination signal via the illumination communication means during the period when the heating element is unpowered but the remaining heat in the furnace supplies heated air sufficient for some vaporization.

The convection heating element shown here as a resistance coil preferable formed of at least one of KANTHAL TM, nichrome, stainless steel and titanium. In some instances ceramic heaters or high-temperature co-fired ceramics (HTCC) with metal element layered therein or thereon may be used in place of the coiled wire. Preferably the systems has a peak power of above 100 Watts, more preferably above 200 Watts. Most preferably the system peak power exceeds 250 Watts.

Figure 4:
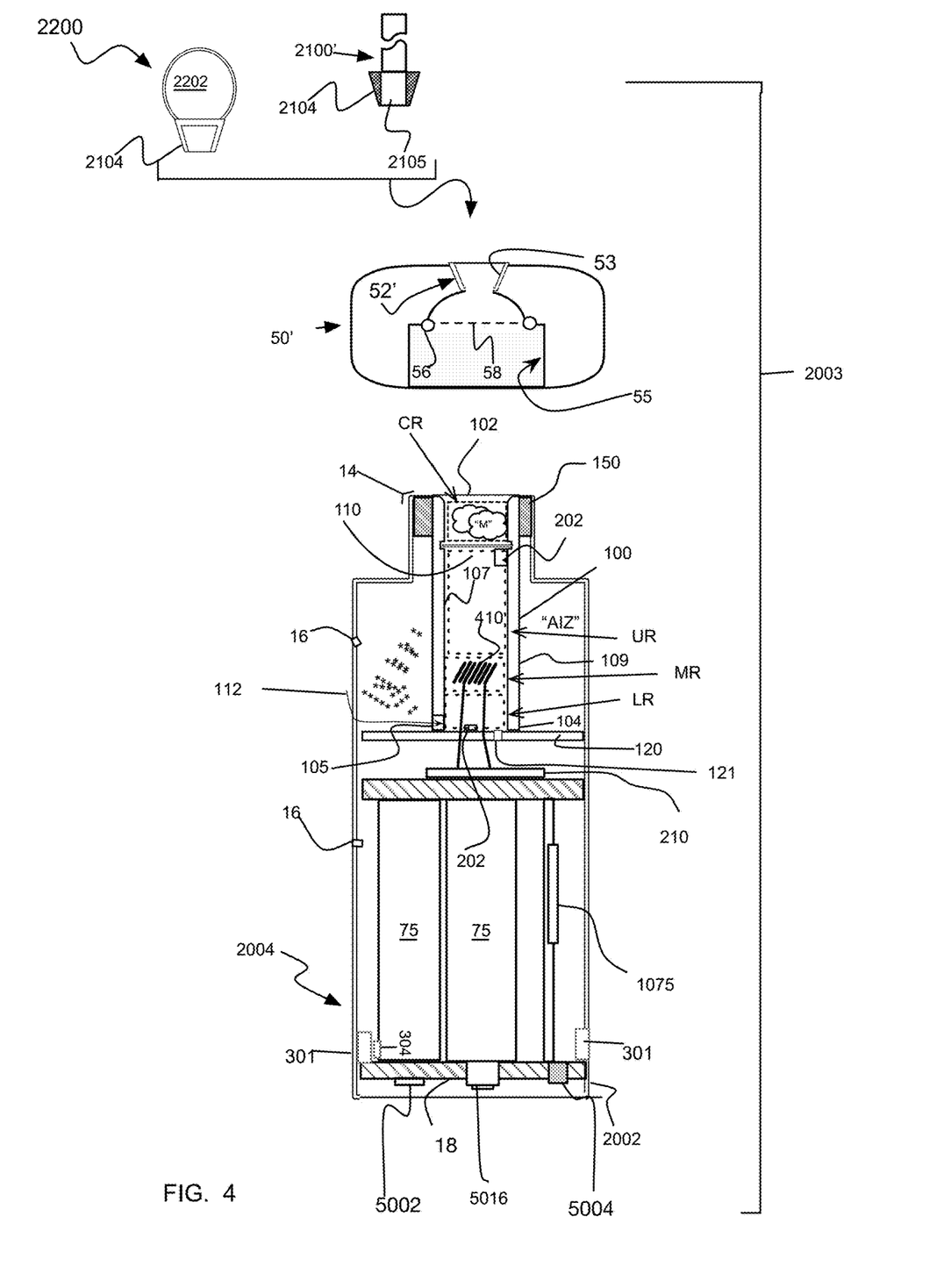

FIG. 4 shows aspects of convection vaporizers with unitary furnace and material chambers 2003. The body 2004 is generally hollow, the bottom of the body 2002 is formed at least partially open. Affixed within the body inset from the bottom 2002 is a bottom plate 18 which partially seals the body's bottom and is a support for a main power on/off switch 5002 and one or more input outputs such as date line and recharge connection 5004 and an on/off control configured as a switch or push button 5016 which starts a heating cycle for use. Each switch or input is in signal communications with the controller. The recharge input may be in signal communications with a recharge controller (PCB) 1075 or the controller 210. In this implementation a heating on/off switch 5006 is affixed on the exterior of the body and is in signal communication with the Controller 210. A battery power supply 75 is placed within the body and is in electrical communication with the recharge connection 5004 and the controller 210 which includes the necessary circuitry such as a mosfet for switching the power from battery supply to heating element per the microprocessor "MP" and software thereon.

In this exemplary the illumination communication means is a lens 301 and which encircles at least ½ of the body and a series of LED (304) directed at the ring whereby the LEDs provide illumination to the lens and the lens is configured to diffuses and/or displays the illumination. The LEDS being in signal communication with the controller and controlled thereby.

A cover (50') is configured with an inner annular wall (55) and is configured to removably partially seal and fits over the open top 14 of the body and the top 102 of the unitary convection furnace and material chamber. A gasket 56 inside the cover can be added to improve the seal. The top 102 of the unitary convection furnace and material chamber is surrounded with an insulator 150 to both fix it in place and provide a surface to seal against the annular wall and top of the cover. A screen 58 may be added to reduce any vaporizing material "M" passing from the device into the fluid passage 52' having a first interface profile 53 that mates reversibly with the second interface profile 2104 having a fluid pass through 2105 which fluidly connects to the user interface 2100'. A closure 2200 to seal off the fluid passage 52' has a second interface profile 2104 to mates with the first interface profile 53 an optional finger grab 2202 may be added for easy of placement and removal.

Figure 3:
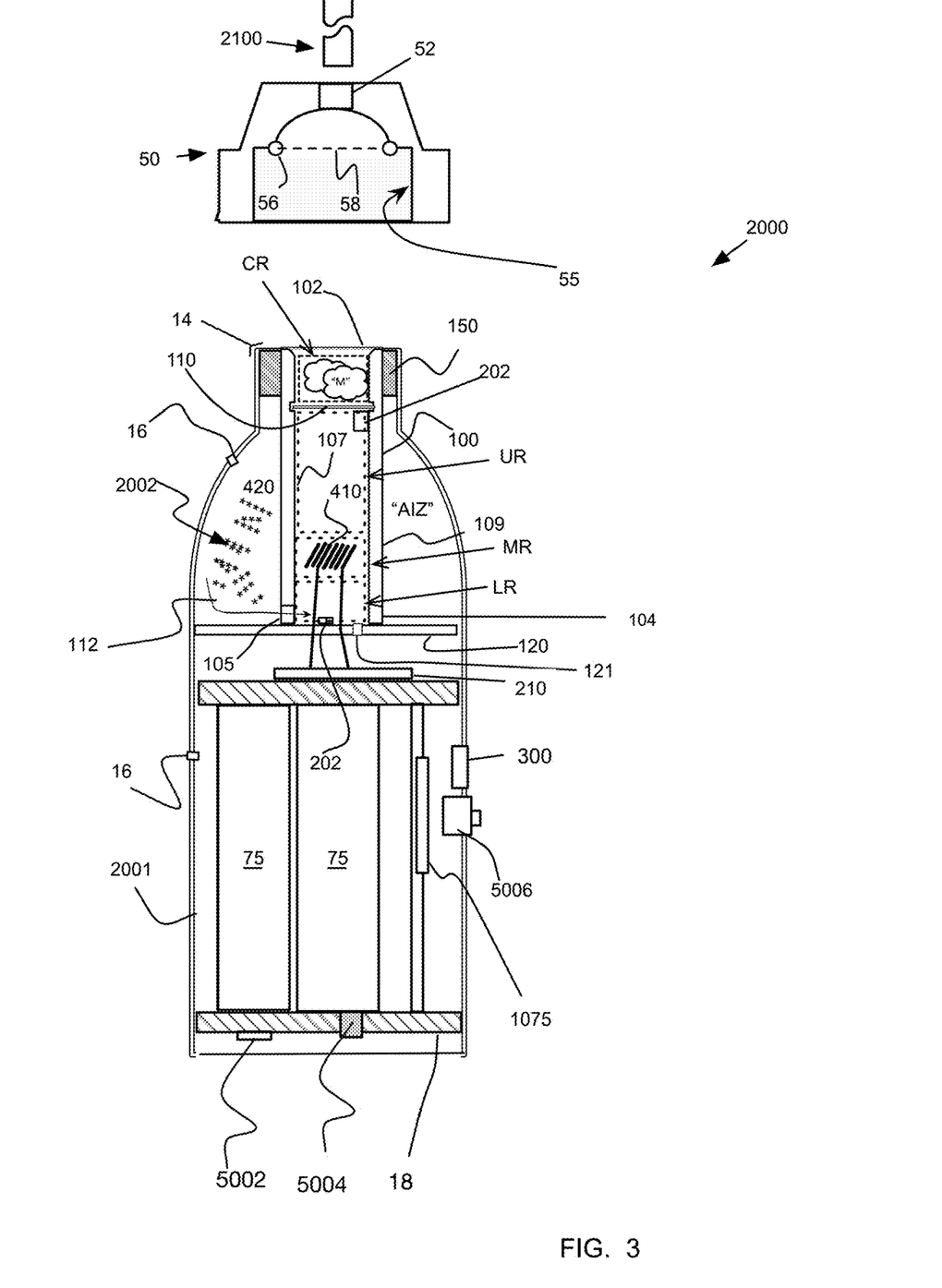
FIGS. 3 and 4 illustrates convection vaporizers with unitary furnace and material chamber; and, FIGS. 5A and 5B illustrates a partial view of aspects of convection vaporizers with unitary furnace and material chamber with attachable storage module.
Figures 5A, 5B:
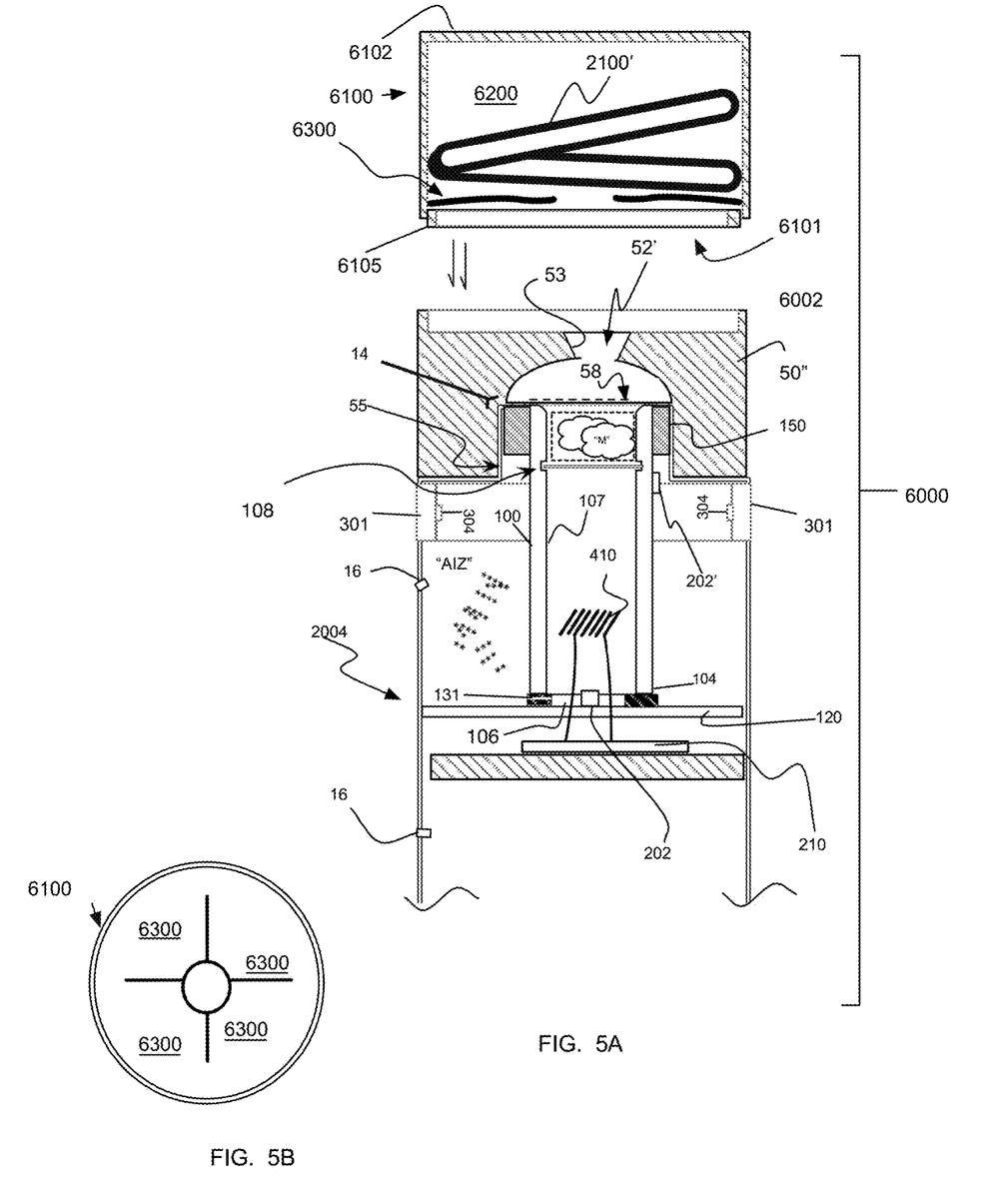

FIGS. 5A and 5B shows a partial view of aspects of convection vaporizers with unitary furnace and material chamber. The body 2004 is generally hollow, the bottom of the body is formed at least partially open. The electrical and thermal components shown in FIGS. 3 and 4 are not shown in these figures for the sake of brevity. Rather, focus in these figures is on the beneath the unitary furnace and material chamber vent 106 formed by one or more gaskets 131 which raise the bottom 104 of above the floor and the nesting cap structure. In this exemplary the illumination communication means is a ring lens 301 and which encircles at least ½ of the body and a series of LEDs 304 directed at the ring. The LEDs being in signal communication with the controller and controlled thereby.

A cover 50" with inner annular wall 55 reversibly and partially seals and fits over the open top 14 of the body and the top of the unitary convection furnace and material chamber. A gasket inside the cover can be added to improve the seal. The top of the unitary convection furnace and material chamber is surrounded with an insulator to both fix it in place and provide a surface to seal against the cover. A screen 58 may be added to reduce any vaporizing material "M" passing from the device into the fluid passage 52' having a first interface profile 53 that mates reversibly with the second interface profile having a fluid passage which fluidly connects to the user interface. (shown in FIG. 4). The fluid passage may be referred to as a top fluid passage or top fluid passageway. At the top surface of the cover 50" is a storage module interface catch 6002. A storage container 6100 is configured to reversibly mate with the interface catch. The container 6100 which has a generally hollow interior 6200 an open bottom 6101 and a sealed top 6102. A storage module latch 6105 is shown on the open bottom of the storage module. In some instances the latch and catch is a friction fit, in other instances a threaded interface or magnetic latch may be used.

The storage module may be partially closed near the latch with flexible flaps 6300. The flexible flaps prevent or limit items in the storage module from falling out if the storage module is removed. It is envisioned that a user may store a flexible user interface 2100' coiled inside the storage module to limit disassociation of parts from the system and reduce odor associated with the user interface from the essential oils.

Those of ordinary skill in the art will recognize that there are a plethora of latch and catch combinations to reversibly connect the accessory module to the body and that a mere design alteration would be within the scope of this disclosure.

While the method and agent have been described in terms of what are presently considered to be the most practical implementations and aspects thereof, it is to be understood that the disclosure need not be limited to the disclosed implementations, aspects or order and/or sequence of combination of aspects. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the implementation, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternatives.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps. Such terms should be interpreted in their most expansive forms so as to afford the applicant the broadest coverage legally permissible. All callouts associated with figures are hereby incorporated by this reference.

Since certain changes may be made in the above system, method, process and or apparatus without departing from the scope of the disclosure herein involved, it is intended that all matter contained in the above description, as shown in the accompanying drawing, shall be interpreted in an illustrative, and not a limiting sense.

It will be understood that various aspects or details of the disclosures may be changed combined, or removed without departing from the scope of the invention. It is not exhaustive and does not limit the claimed inventions to the precise form disclosed. Furthermore, the foregoing description is for the purpose of illustration only, and not for the purpose of limitation. Modifications and variations are possible in light of the above description or may be acquired from practicing the invention. The claims and their equivalents define the scope of the invention.

I claim:

1. A convection portable aromatherapy vaporizing system comprising:
   a power supply (75);
   a heating system comprising;
   a unitary furnace (100) with an open top (102) and bottom end comprising;
   a material region "CR";
   an upper region "UR";
   a mid region "MR";
   a lower region "LR';
   wherein the material chamber is formed by dividing the unitary furnace with an air permeable divider (110);
   a floor (120) configured to at least partially seal off the bottom end of the unitary furnace;
   a heating element (410) inside the mid region "MR";
   a temperature sensor (202) fixed in close proximity to the floor within the unitary furnace;
   a controller (210) in signal communication with at least the sensor, heating element, power supply and on/off control (5016); and,
   wherein at least a portion of air heated by the heating element during vaporization of material (M) enters the bottom (104) of the unitary furnace from an air insulation zone "AIZ" surrounding the exterior of the unitary furnace.

2. The convection vaporizing system of claim 1 further comprising:
   a generally hollow body (2004) with an open top (14) at one end surrounding the open top of the unitary furnace;
   at least the heating system and power supply are within the hollow body;
   a cover which partially seals the open top of the body; and,
   wherein the open top of the body and open top of the unitary furnace are coaxially aligned.

3. The convection vaporizing system of claim 2 wherein the cover is configured with an inner annular wall (55) and is configured to removably partially seal and fits over the open top (14) of the body and the top (102) of the unitary convection furnace and material chamber.

4. The convection vaporizing system of claim 3 further comprising:
   a fluid passage (52') through the cover;
   a first interface profile (53) formed at the fluid passage;

a user interface (2100') with a second interface profile (2104) configured to fluidly connect to the cover.

5. The convection vaporizing system of claim 2 further comprising at least one illumination communication means (301) in signal communication with the controller configured to produce an illumination visible on the body.

6. The convection vaporizing system of claim 5 wherein the illumination means further comprises a lens and LEDs (304) configured to illuminate said lens.

7. The convection vaporizing system of claim 1 further comprising a catch (108) formed in an inside wall (107) of the unitary furnace configured to mate with the air permeable divider.

8. The convection vaporizing system of claim 4 further comprising a closure (2200) to seal off the fluid passage (52) configured with a second interface profile (2104) to mates with the first interface profile.

9. The convection vaporizing system of claim 1 wherein:
the heating on/off control (5016) is in signal communication with the controller; and,
wherein pushing the on/off control initiates a heating cycle.

10. The convection vaporizing system of claim 2 further comprising:
a storage module interface catch (6002) formed on the cover; and,
a storage container (6100) configured to reversibly mate with the interface catch by way of a storage module latch (6105).

11. A method to deliver aliquots of heated air to material, the method comprising:
forming a material region (CR) in an unitary furnace having an exterior, open top and open bottom by dividing the unitary furnace with an air permeable divider and placing material "M" in the CR;
partially sealing off the open bottom of the unitary furnace with a floor;
partially sealing off the open top of the unitary furnace;
providing a fluid communication for air to enter the bottom of the unitary furnace;
a controller selectively providing electrical power to a heating element within the unitary furnace configured to heat air in at least an upper region (UR) of the unitary furnace;
providing a top fluid passage in communication with the top of the unitary furnace;
applying suction to the top fluid passage; and,
wherein heated air passes into the material and vaporizes organic oils; and,
wherein vaporized material is withdrawn from the top fluid passage.

12. The method of claim 11 to deliver aliquots of heated air to material in a unitary furnace, the method further comprising temperature sensor (202) in signal communication with the controller fixed in close proximity to the floor within the unitary furnace; and,
wherein the controller controls the electrical power supplied to the heating element at least in part based on the temperature sensor input to the controller.

13. The method of claim 11 to deliver aliquots of heated air to material in a unitary furnace the method further comprising the controller selectively signals the user with LED (304) illumination passing through a lens.

14. The method of claim 13 to deliver aliquots of heated air to material in a unitary furnace wherein the signal to the user displays status of a state of the heating and vaporizing system.

* * * * *